(12) United States Patent  (10) Patent No.: US 8,665,096 B2
Rantala et al.  (45) Date of Patent: Mar. 4, 2014

(54) ALARM CONTROL METHOD, PHYSIOLOGICAL MONITORING APPARATUS, AND COMPUTER PROGRAM PRODUCT FOR A PHYSIOLOGICAL MONITORING APPARATUS

(75) Inventors: Borje Rantala, Helsinki (FI); Mikko Kaski, Espoo (FI)

(73) Assignee: General Electric Company, Schenectady, NY (US)

( * ) Notice: Subject to any disclaimer, the term of this patent is extended or adjusted under 35 U.S.C. 154(b) by 483 days.

(21) Appl. No.: 12/974,426

(22) Filed: Dec. 21, 2010

(65) Prior Publication Data

US 2012/0154152 A1  Jun. 21, 2012

(51) Int. Cl.
*G08B 23/00* (2006.01)
(52) U.S. Cl.
USPC ............... 340/573.1; 600/323; 600/508
(58) Field of Classification Search
USPC ............................................ 340/573.1
See application file for complete search history.

(56) References Cited

U.S. PATENT DOCUMENTS

| | | |
|---|---|---|
| 4,584,880 A | 4/1986 | Matzuk |
| 4,676,105 A | 6/1987 | Matzuk |
| 5,261,280 A | 11/1993 | Matzuk |
| 5,394,750 A | 3/1995 | Matzuk |
| 5,846,190 A | 12/1998 | Woehrle |
| 5,865,736 A | 2/1999 | Baker et al. |
| 6,574,716 B2 | 6/2003 | Dovi |
| 6,602,201 B1 | 8/2003 | Hepp et al. |
| 6,684,090 B2 | 1/2004 | Ali et al. |
| 6,725,074 B1 | 4/2004 | Kaestle |
| 6,742,399 B2 | 6/2004 | Kunz et al. |
| 7,251,524 B1 | 7/2007 | Hepp et al. |
| 7,598,878 B2 | 10/2009 | Goldreich |
| 7,628,339 B2 | 12/2009 | Ivri et al. |
| 8,115,640 B2 | 2/2012 | Walls |
| 8,374,666 B2 * | 2/2013 | Graboi et al. ............ 600/323 |
| 8,401,607 B2 * | 3/2013 | Mannheimer ............ 600/323 |

(Continued)

FOREIGN PATENT DOCUMENTS

WO 2009093159 A1 7/2009

OTHER PUBLICATIONS

Pending U.S. Appl. No. 12/787,949 , entitled "Alarm Generation Method for Patient Monitoring, Physiological Monitoring Apparatus, and Computer Program Product for a Physiological Monitoring Apparatus", Borje Rantala, filed May 26, 2010.

(Continued)

*Primary Examiner* — Kerri McNally
(74) *Attorney, Agent, or Firm* — Andrus Intellectual Property Law, LLP (57) ABSTRACT

A method for controlling alarms in a physiological monitoring apparatus, a physiological monitoring apparatus, and a computer program product for a physiological monitoring apparatus are disclosed. In order to decrease the number of nuisance alarms, the level of a physiological signal obtained from a subject is observed and signal morphology is determined for the physiological signal in response to detecting a change of the level of the physiological signal to a predetermined value range representing low signal values, thereby to obtain reference morphology for the physiological signal. Signal morphology is monitored if the physiological signal remains in the predetermined value range and alarms are suppressed as long as the signal morphology fulfills predefined criteria with respect to the reference morphology and the level of the physiological signal remains in the predetermined value range.

17 Claims, 3 Drawing Sheets

(56) References Cited

U.S. PATENT DOCUMENTS

| | | |
|---|---|---|
| 2002/0007685 A1 | 1/2002 | Kunz et al. |
| 2002/0035315 A1 | 3/2002 | Ali et al. |
| 2004/0236187 A1 | 11/2004 | Bock et al. |
| 2007/0167753 A1 | 7/2007 | Van Wyk et al. |
| 2007/0167850 A1* | 7/2007 | Russell et al. ............... 600/513 |
| 2007/0249954 A1 | 10/2007 | Virag et al. |
| 2007/0249955 A1 | 10/2007 | Carlson et al. |
| 2007/0249956 A1 | 10/2007 | Carlson et al. |
| 2007/0265544 A1 | 11/2007 | Carlson et al. |
| 2008/0046024 A1 | 2/2008 | Carlson et al. |
| 2008/0157980 A1 | 7/2008 | Sachanandani et al. |
| 2008/0228052 A1 | 9/2008 | Al-Ali |
| 2008/0269835 A1 | 10/2008 | Carlson et al. |
| 2008/0287756 A1 | 11/2008 | Lynn |
| 2008/0306397 A1 | 12/2008 | Bonmassar et al. |
| 2010/0016691 A1 | 1/2010 | Watson et al. |
| 2010/0022903 A1* | 1/2010 | Sitzman et al. ............... 600/509 |

OTHER PUBLICATIONS

Search Report and Written Opinion from EP Application No. 11192710.9, dated Nov. 7, 2012.

Search Report and Written Opinion from EP Application No. 11166744.0, dated Jan. 4, 2013.

* cited by examiner

ALARM CONTROL METHOD, PHYSIOLOGICAL MONITORING APPARATUS, AND COMPUTER PROGRAM PRODUCT FOR A PHYSIOLOGICAL MONITORING APPARATUS

BACKGROUND OF THE INVENTION

This disclosure relates generally to patient monitoring. More particularly, the present invention relates to control of alarm generation in physiological monitoring apparatuses, termed patient monitors below.

Patient monitors are electronic devices designed to display physiological information about a subject. Electrocardiogram (ECG), electroencephalogram (EEG), plethysmographic signals, and signals related to blood pressure, temperature, and respiration represent typical physiological information contained in full-size patient monitors. Patient monitors are typically also furnished with alarming functionality to alert the nursing staff when a vital sign or physiological parameter of a patient exceeds or drops below a preset limit. Alarms are normally both audible and visual effects aiming to alert the staff to a life-threatening condition or to another event considered vital.

In addition to individual sensor/parameter alarms, patient monitors may be configured to raise combinatory alarms. That is, several physiological parameters may be used to determine a combined index and to give an alarm when the combined index fulfills a specific criterion. The combinatory alarms may range from simple combinations like "low heart rate and low arterial pressure" to complex rule-based scenarios used in various clinical support systems, for example. Below, the term physiological parameter is used to refer to the physiological variable to be monitored. As discussed above, the variable may be an individual parameter, such as heart rate or blood pressure, or a combinatory variable/index derived from multiple individual parameters. An individual physiological parameter may also represent a waveform signal value determined over a predefined period of time.

In most monitors, the alarm limits of a physiological parameter may be defined by the user, since the limits typically depend on patient etiology, age, gender, medication, and various other subjective factors. Each physiological parameter may also be assigned more than one alarm limit/criterion. That is, for a specific physiological parameter a patient monitor may raise alarms of different levels.

The monitor may also be provided with an alarm escalation mechanism to escalate unacknowledged and/or persistent alarms. Typically, an alarm is raised when the physiological parameter reaches a predefined first alarm limit, and the level of priority/severity of the alarm is increased if the alarm persists and/or remains unacknowledged for a predetermined period of time. The escalation rules stored in the monitor define how an alarm is escalated. Each alarm level may involve different alarming functionality.

In a clinical environment, one problem is alarming for weak signals. Many of the physiological signals measured from the patient are weak in nature and thus also extremely vulnerable to interference. Furthermore, the level of a physiological signal may drop significantly due to an external reason. For example, the level of an ECG signal may drop when the patient turns in bed or the level of a plethysmographic signal may drop when the patient is subject to a clinical operation that causes pain. Monitoring such weak signals in a noisy environment makes alarm generation a demanding task, as the monitor should be both sensitive and specific in raising alarms. That is, the monitor should be able to recognize all true alarm events, without raising false or clinically irrelevant alarms. During low signal level, the patient monitor should be able to detect real alarm events in which the signal level is low, such as asystole, but if the patient monitor is made sensitive enough for such events, noise and interference tend to increase the number of false alarms, or worse, cause the monitor to miss a real asystole alarm due to noise triggering the heart heat counter. Nuisance alarms are thus increased when the level of the signal is lower than normal, since the patient monitor may alert of the lowered signal level (regarded as a possible alarm) and since the quality/confidence of the parameter calculation is lowered during periods of lowered signal level. Due to the lowered quality/confidence, the number of events of the physiological parameter only slightly crossing the lowest priority threshold, and thus also the number of clinically irrelevant alarms, is increased during periods of lowered parameter confidence.

Due to the above difficulties, in a real clinical environment a large fraction of the alarms, even most alarms, may be false or at least clinically irrelevant. Such a large number of false or irrelevant alarms causes an enormous burden on the nursing staff and may also lead to impairment of the responses to true alarms. Therefore, reducing the amount of false or clinically irrelevant alarms is central to patient monitoring.

BRIEF DESCRIPTION OF THE INVENTION

The above-mentioned problem is addressed herein which will be comprehended from the following specification. In order to decrease the number of clinically irrelevant alarms, signal level is monitored while monitoring proceeds in normal monitoring mode. If low signal level is detected and if continuation of the patient monitoring is still acceptable despite the lowered signal level, the monitoring process changes from the normal mode to a special mode termed low signal monitoring mode, in which nuisance alarm events are eliminated or reduced. In connection with the mode change, signal morphology is determined to obtain reference morphology that characterizes the morphology of the signal at the time of the detection of the low signal level. The monitoring process remains in the low signal monitoring mode as long as the signal level remains low and the signal morphology fulfills predetermined criteria in relation to the reference morphology. Normal monitoring mode is restored if the signal morphology does not any more fulfill the said criteria or if the signal returns to normal level. In the low signal monitoring mode, nuisance alarms may be eliminated or reduced by modifying the normal monitoring mode so that the effect of the lowered signal level on generation of nuisance alarms is suppressed. However, the suppression of nuisance alarms does not mask relevant alarms that may occur during periods of lowered signal level. This is because normal monitoring mode is restored if a significant change occurs in the morphology during the low signal monitoring mode. Consequently, important alarm events featuring low signal level, such as asystole, cannot be masked by the alarm suppression operation carried out in the low signal monitoring mode.

In an embodiment, method for controlling alarms in a physiological monitoring apparatus comprises observing the level of a physiological signal obtained from a subject and determining, in response to detecting a change of the level of the physiological signal to a predetermined value range representing low signal values, signal morphology for the physiological signal, thereby to obtain reference morphology for the physiological signal. The method further includes monitoring the signal morphology when the physiological signal remains in the predetermined value range and suppressing alarms when the signal morphology fulfills predefined criteria with respect to the reference morphology and the level of the physiological signal remains in the predetermined value range.

In another embodiment, a physiological monitoring apparatus comprises a signal level monitoring unit adapted to monitor the level of a physiological signal obtained from a subject and a morphology determination unit adapted to determine signal morphology for the physiological signal, thereby to obtain reference morphology for the physiological signal. The apparatus further includes a morphology monitoring unit adapted to monitor whether the signal morphology fulfills predefined criteria with respect to the reference morphology and an alarm mode control unit adapted to suppress alarms when the signal waveform morphology fulfills the predefined criteria with respect to the reference morphology and when the level of the physiological signal remains in a predetermined value range representing low signal values.

In a still further embodiment, a computer program product for a physiological monitoring apparatus comprises a first program product portion configured to monitor a level of a physiological signal obtained from a subject and a second program product portion configured to determine signal morphology for the physiological signal, thereby to obtain reference morphology for the physiological signal. The computer program product further comprises a third program product portion configured to monitor whether the signal morphology fulfills predefined criteria with respect to the reference morphology and a fourth program product portion configured to suppress alarms when the signal waveform morphology fulfills the predefined criteria with respect to the reference morphology and the level of the physiological signal remains in a predetermined value range representing low signal values.

Various other features, objects, and advantages of the invention will be made apparent to those skilled in the art from the following detailed description and accompanying drawings.

DETAILED DESCRIPTION OF THE INVENTION

Figure 1:
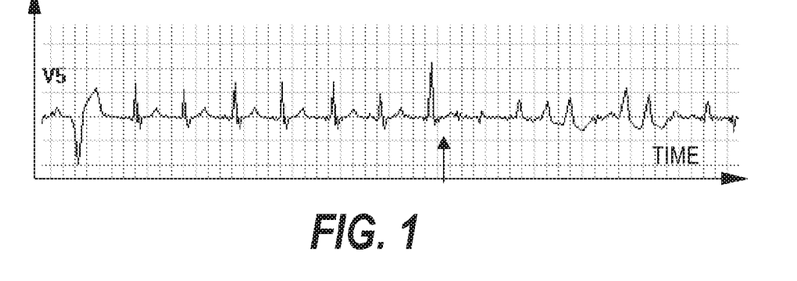
FIG. 1 illustrates a significant change in the amplitude of an ECG lead signal.
Figure 2:
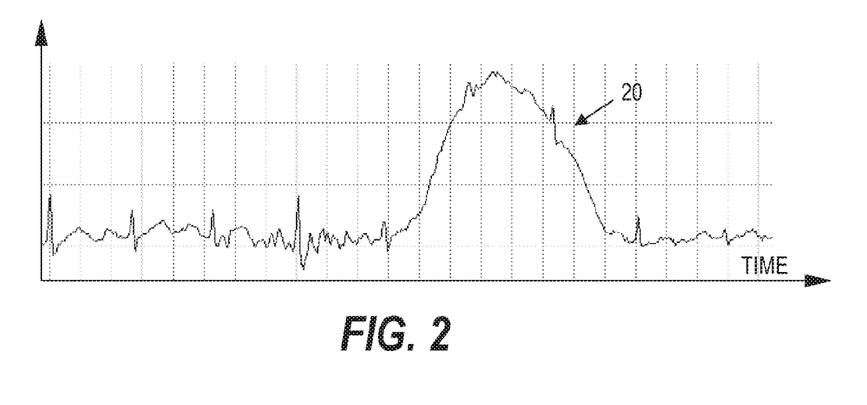
FIG. 2 illustrates an example of a change in ECG lead amplitude when a patient turns in bed.
Figure 3:
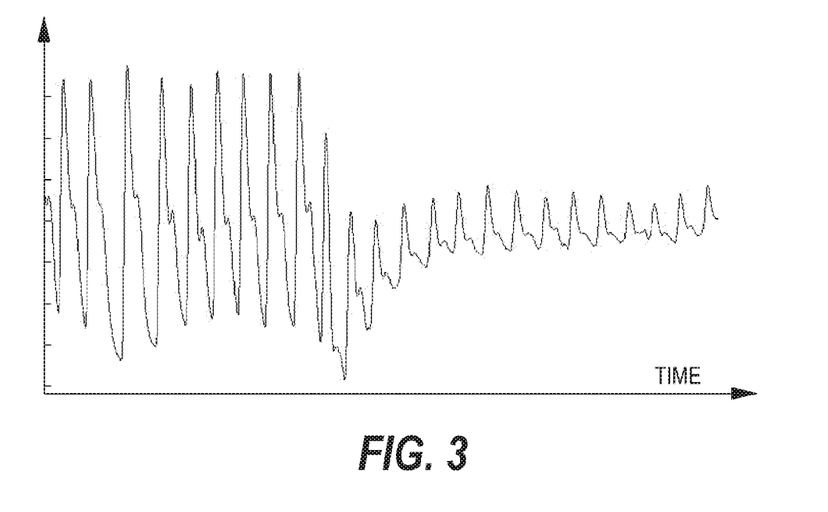
FIG. 3 illustrates a sudden drop in a plethysmographic signal due to vasoconstriction.

In clinical environment, the amplitude of a physiological signal measured from a subject may change suddenly. Sometimes the change is significant, sometimes not. For example, the amplitude of an ECG signal may drop due to various physiological reasons, but also due to a problem in the placement of the electrodes, for example, or due to a change in the posture of the patient. FIG. 1 illustrates a physiologically significant change in the amplitude of an ECG channel signal. The approximate moment of change is indicated by an arrow in the figure. FIG. 2 illustrates a change in an ECG lead signal when the patient turns in bed. The motion of the patient causes a swing 20 in the baseline of the signal. Simultaneously the actual signal level, i.e. amplitude with respect to the baseline, diminishes. A plethysmographic signal may drop significantly due to "cold fingers" (not dangerous in general) or due to a collapsing hemodynamic state, for example. FIG. 3 illustrates a sudden drop in the amplitude of a plethysmographic signal due to vasoconstriction. Such a drop may also occur, for example, as a result of an incision causing pain.

To detect this kind of unexpected level changes, the level of the physiological signal is monitored substantially constantly. The physiological signal here refers to a certain type of a signal, such as ECG signal. That is, the physiological signal may comprise several lead signals or measurement channels. The level in turn refers to the amplitude or power of the physiological signal, determined in relation to the baseline of the signal. The physiological signal is typically an ECG signal or a (photo)plethysmographic signal, but may be any physiological waveform signal obtained from a subject for monitoring the state of the subject. In connection with the examples discussed below it is assumed that the physiological signal is an ECG signal.

Figure 4:
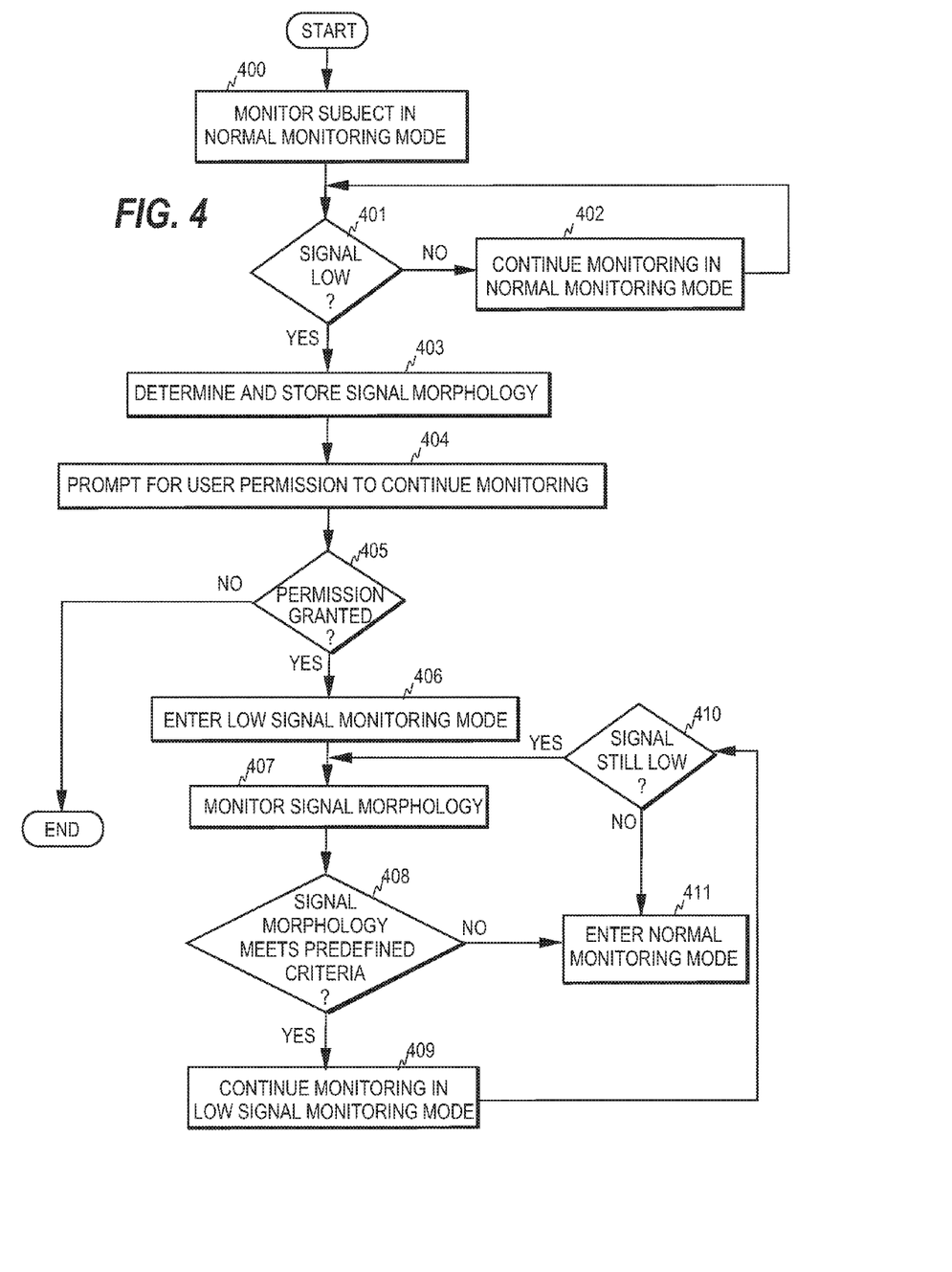
FIG. 4 illustrates one embodiment of a monitoring method that may be used to decrease the number of irrelevant alarms.

FIG. 4 illustrates one embodiment of a method for monitoring a subject/patient. As long as the level of a physiological signal, i.e. the amplitude compared to the baseline, remains in a value range considered as normal range, the monitoring proceeds normally using normal alarm generation, cf. steps 400-402. During this normal monitoring mode signal level is monitored and if it is detected in step 401 that the level of the signal drops to a predetermined value range representing low signal values, current signal morphology is determined and the obtained morphology is stored as reference morphology (step 403). The predetermined value range depends on the signal and various time constants may be used to prevent transient drops from causing detection of low signal level. For an ECG signal, the amplitude of the QRS complex, for example, may be measured and if the amplitude is in a predetermined low range, such as 0.15-0.25 mV, the signal level is considered low. In step 403, the current morphology of the QRS complex may be determined by determining a predetermined set of QRS parameters, such as QRS amplitude, QRS duration, ventricular activation time, and Q wave amplitudes and durations. The stored QRS parameter set defines the morphology of the QRS complex at the time of detection of the lowered signal level and thus forms the reference morphology.

When low signal level is detected in step 401, the monitoring process changes to another mode termed low signal monitoring mode in this context. However, before the mode change a decision needs to be made whether or not the state of the subject allows the monitoring process to enter the low signal monitoring mode in which the number of alarms caused by the low signal is reduced, thereby to reduce the number of nuisance alarms. In other words, since the low signal level may be caused by different external or physiological reasons, it is to be checked, upon detection of low signal level, that the lowered signal is not caused by a significant physiological reason requiring urgent measures and thus possibly also stopping of the monitoring.

The decision may be made automatically by the patient monitor, if the monitoring process clearly indicates that the state of the patient allows the monitoring to be continued. However, typically the user of the monitor is requested to check the current state of the patient and to make the decision on the activation of the low signal monitoring mode. Consequently, an alarm or a notification requesting for a permission to continue the monitoring is displayed to the user in step 404 in response to the detection of the low signal level. Here, a dialog window may be opened on the screen of the monitor, with a warning of a possible physiological reason causing the low signal level. In case of an ECG signal, for example, the dialog window may include a warning of a possible asystole with a request to check whether real asystole or small QRS (i.e. low signal level) is involved. If the user selects "small QRS", the low signal monitoring mode is entered. Here, the user may also be given a chance to select from different low signal monitoring modes, in which the alarm events are reduced in different ways.

Thus, if the user gives a permission to continue monitoring, the user confirms that no physiological reason hinders continued monitoring and also accepts that the reliability of the physiological parameter(s) determined may be compromised due to the lowered signal level.

The determination of the reference morphology may also be repeated if the user input lingers or the determination may be made only after the user permission is received; it is essential that the permission to continue and the determination of the reference morphology are temporally close to each other, so that the reference morphology characterizes the signal morphology at the time of receipt of user permission.

In response to the positive decision to continue the monitoring, the low signal monitoring mode is entered in step 406. In this mode, alarms are eliminated or the number of alarms is reduced as long as the signal level remains low and certain morphology criteria are met that may be checked based on current signal morphology and the reference morphology. More particularly, signal morphology is monitored substantially continuously in the low signal monitoring mode (step 407) and the monitoring process remains in this mode as long as the signal level remains low and the signal morphology fulfills predetermined criteria with respect to the reference morphology, cf. steps 408-411. Typically, the monitoring process remains in this mode as long as the signal morphology remains substantially equal to the reference morphology.

Thus, upon entering the low signal monitoring mode, continuous signal morphology determination is started and current signal morphology is compared with the reference morphology determined earlier, cf. steps 407 and 408. If the signal level is still low but it is detected that the signal morphology does not any more fulfill the predetermined criteria with respect to the reference morphology, normal alarm mode is entered (step 408/no and step 411). A similar mode change occurs if the signal level returns to a value range considered as normal (step 410/no), regardless of the morphology. However, normally there is also a change in the morphology when the signal level returns to normal range.

In the low signal level mode, nuisance alarms are eliminated by an appropriate mechanism. In one mechanism, which may be used in case of an ECG signal, for example, the sensitivity of the patient monitor is increased by lowering the signal threshold that causes a "small QRS" alarm. That is, this embodiment of the low signal monitoring mode corresponds to the normal monitoring mode, except that the signal threshold causing a "small QRS" alarm is lowered, thereby to eliminate the reasons causing "small QRS" alarms (i.e. false asystole alarms). The monitoring process then follows the QRS sequence without alarming of the small QRS. However, a possible asystole event cannot be masked, since normal monitoring mode is restored once the morphology changes substantially.

In another mechanism alarms are delayed based on a quality measured derived from the signal level. In this embodiment, the delaying is carried out by controlling the escalation of an alarm based on the quality measure. When it is detected in the low signal monitoring mode that the first alarm limit is reached, an alarm escalation process is started. Since the priority of the alarm related to the first alarm limit is typically low, the alarm may be indicated in a non-disturbing manner at the bedside or at another site where a caregiver may easily acknowledge it. It is also possible that no indication of the low priority alarm is given to the caregiver, but the caregiver is informed of an alarm only later if the priority of the alarm is increased. The lowest priority alarm event may thus be hidden. The rate of the alarm escalation process started upon detection of the crossing of the first alarm limit may be directly proportional to the quality measure, i.e. the lower the signal level the lower the escalation rate. Since the number of events of the physiological parameter only slightly crossing the lowest priority threshold is high during periods of lowered parameter reliability (i.e. during low signal level), the quality/level based control of the alarm escalation may greatly reduce the number of alarms caused by such events, since the escalation control hampers the escalation of such alarms to higher priority alarms that would be clinically irrelevant.

In other words, this embodiment of the low signal monitoring mode, which may be used for a plethysmographic signal, for example, corresponds otherwise to the normal monitoring mode, except that alarm escalation rate is decreased with respect to the normal mode. Decreased escalation rate delays the alarms and hampers the escalation of false alarm events to clinically irrelevant alarms. The decreased escalation rate of the low signal monitoring mode may be fixed or may depend on the current signal level. For example, the crossing of the first alarm limit may correspond to a hidden alarm and the escalation rate of the low signal monitoring mode may be half of the escalation rate used in the normal monitoring mode.

In further embodiments of the low signal monitoring mode, combinations of the sensitivity increase and alarm delay may be used.

In the above embodiments, signal morphology is determined based on one physiological signal or a section thereof, such as the QRS complex of the ECG signal. In addition to the QRS complex, other physiological waveforms may be used to determine the signal morphology or to provide additional information on the likely reasons causing the restoration of the normal monitoring mode. As the QRS complex is not indicative of the blood pumping action of the heart, an additional waveform indicative of the pumping action of the heart may be used, in addition to the QRS complex, as the waveform information that defines signal morphology. Such an additional waveform may be, for example, an impedance cardiogram (ICG) signal or signal section, a plethysmographic signal or signal section, or an arterial blood pressure signal or signal section, where the signal section includes at least part of the pulse caused by the pumping heart. That is, the reference morphology determined in step 403 may comprise both the morphology of the QRS complex and the morphology of the additional waveform. If it is then detected in the low signal monitoring mode (step 408) that either the QRS complex or the additional waveform has changed substantially from its reference morphology, the normal monitoring mode is restored.

In a further embodiment, the P wave of an ECG signal may be used to improve the information content to be displayed in connection with the restoration the normal monitoring mode. In this case, the reference morphology that dictates the ending of the mode is defined by the QRS complex only. However, a similar reference morphology is determined also for the P wave in step 403, thereby to be able to examine the changes occurred in the P wave. If it is detected in the low signal monitoring mode that the QRS complex has changed substantially, but the morphology of the P wave has not changed, an alarm is raised in connection with the mode change, since the morphology information is now indicative of an atrioventricular block. Thus, the monitor is able to detect the cessation of low QRS complexes and also to prevent the heart rate counter from counting P waves as QRS complexes. In a similar fashion, the counting of pacer pulses as QRS complexes is prevented. Pacer pulses are usually detected and removed from the ECG signal, but this removal is often incomplete, leaving a small "overshoot" that can be counted as a QRS complex in the low signal mode. Now, due to the morphology requirement of the low signal mode, the "overshoots" cannot be taken for QRS complexes.

In step 404, the user may also be given a chance to enter the low signal monitoring mode for a certain time. This may be useful for example when the patient is administered a drug that takes effect in a given time.

Figure 5:
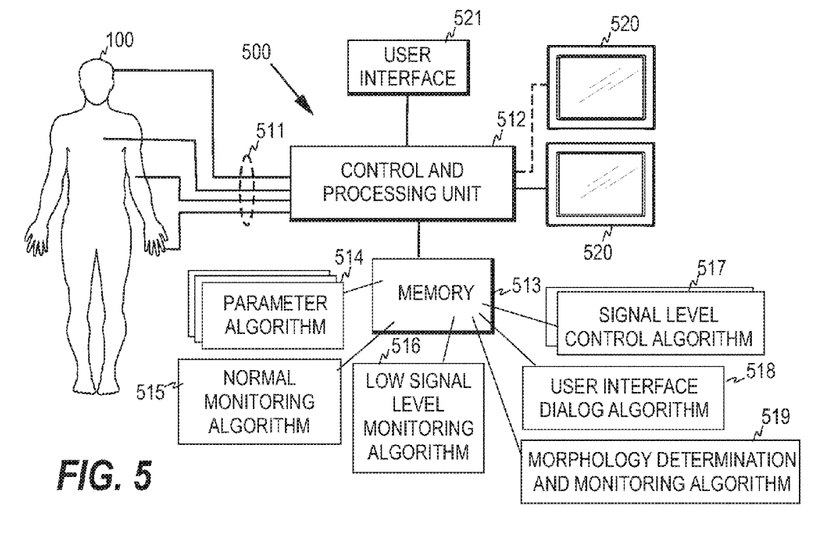
FIG. 5 illustrates an embodiment of a physiological monitoring apparatus that may be used to decrease the number of irrelevant alarms.

FIG. 5 illustrates one embodiment of a physiological monitoring apparatus/system 500 for monitoring a subject 100. A monitoring apparatus/system normally acquires a plurality of physiological channel signals 511 from the subject, where one physiological channel signal corresponds to one measurement channel. The channel signals typically comprise several types of signals, such as ECG, EEG, blood pressure, respiration, and plethysmographic signals. Based on the raw real-time physiological signal data obtained from the subject, a plurality of physiological parameters may be determined, each physiological parameter being calculated from the waveform data of one or more of the physiological channel signals acquired from the subject. If a physiological parameter is derived from more than one physiological channel signal, i.e. from more than one measurement channel, the said channel signals are usually of the same signal type. The physiological parameter may thus also represent a waveform signal value determined over a predefined period of time, although the physiological parameter is typically a distinct parameter derived from one or more measurement channels, such as heart rate derived from one or more ECG channel signals or an $SpO_2$ value derived from one or more plethysmographic channel signals.

The physiological channel signals 511 acquired from the subject are supplied to a control and processing unit 512 through a pre-processing stage (not shown) comprising typically an input amplifier and a filter, for example. The control and processing unit converts the signals into digitized format for each measurement channel. The digitized signal data may then be stored in the memory 513 of the control and processing unit. The digitized signal data is utilized by parameter algorithms 514 adapted to record, when executed by the control and processing unit, the time series of the physiological parameters to be monitored. The obtained time series of the physiological parameters may be stored in the memory. Generally, each physiological parameter may be assigned one or more alarm limits to alert the nursing staff when the parameter reaches or crosses the alarm limit. For example, a physiological parameter, such as heart rate, may be assigned multiple alarm levels of increasing priority/severity and alarm escalation may be used to escalate a low level alarm to the next level of priority/severity, if the low level alarm persists and/or goes unacknowledged long enough.

The control and processing unit uses a signal level control algorithm 517 to examine whether the signal level is normal or low. When the signal is in normal value range, the control and processing unit is in normal monitoring mode and uses a normal monitoring algorithm 515 to monitor the successive values of the parameter and to generate alarms based on the parameter values. This typically involves comparison of the parameter values with at least one alarm limit to detect whether an alarm is to be raised. When a crossing of an alarm limit is detected, the control and processing unit may or may not inform the user of the alarm. In response to the detection of the alarm limit crossing, the control and processing unit may start to escalate the alarm.

When the signal is in a predetermined value range indicating low signal level, the control and processing unit uses a low signal level monitoring algorithm 516 to monitor the successive values of the parameter. As discussed above, this algorithm corresponds otherwise to the normal monitoring algorithm, but is adapted to suppress the effect of the lowered signal level on the generation of nuisance alarms. The control and processing unit further uses a user interface dialog algorithm 518 to obtain user permission for the low signal monitoring mode and a morphology determination and monitoring algorithm 519 to determine and monitor signal morphology. Through algorithms 517-519 the control and processing unit is able to switch between the two monitoring modes. The control and processing unit is further configured to control the display unit(s) 520 of the apparatus. Interaction with users the apparatus/system occurs through user interface 521.

Figure 6:
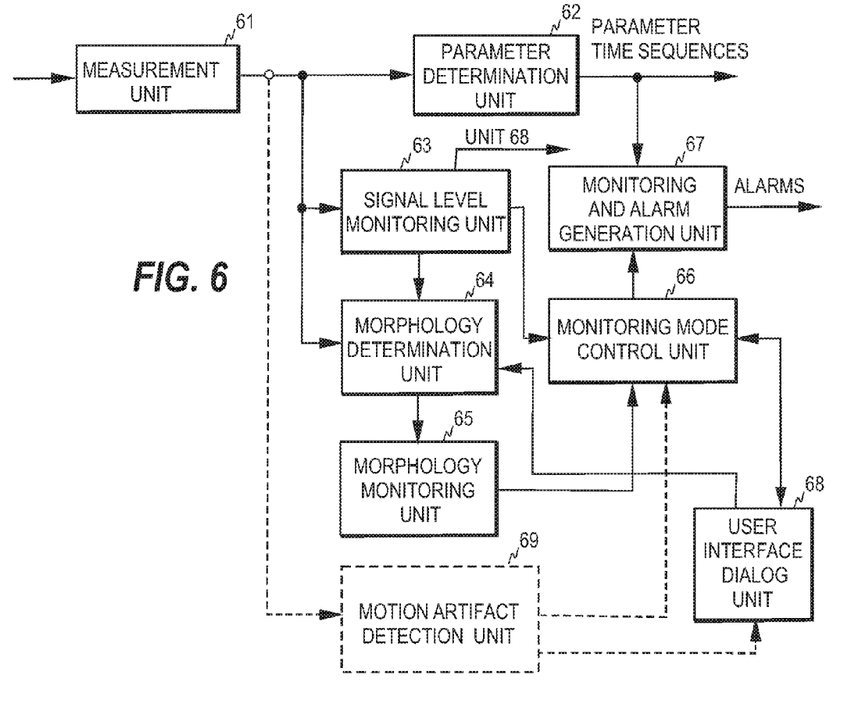
FIG. 6 illustrates an example of the functional entities of the monitoring apparatus in terms of monitoring and alarm generation.

In terms of the monitoring process, the functionalities of the control and processing unit 512 may be divided into the units shown in FIG. 6. A measurement unit 61 is configured to measure the physiological signal data from the subject. A parameter determination unit 62 is configured to determine, based on at least one physiological signal, the physiological parameter(s) to be monitored. A signal level monitoring unit 63 is adapted to monitor the signal level and to activate/deactivate a morphology determination unit 64 adapted to determine signal morphology. Current signal morphology is compared with reference morphology in a morphology monitoring unit 65 configured to examine whether current signal morphology fulfills predefined criteria with respect to the reference morphology. A monitoring mode control unit 66 controls a monitoring and alarm generation unit 67 based on the data obtained from the signal level monitoring unit, from the morphology monitoring unit and from a user interface dialog unit 68, thereby to use either normal or low signal monitoring mode in unit 67. As unit 67 generates alarms according to the monitoring mode indicated by unit 66, the said two units together form the entity that carries out the alarm suppression. This entity is termed an alarm mode control unit in this context. The signal level monitoring unit 63 may also be operatively connected to the user interface dialog unit to activate the morphology determination unit 64 conditionally depending on user input.

As mentioned above, the decision on the introduction of the low signal monitoring mode may also be made automatically if the state of the patient at the time of the detection of the low signal level indicates that the low signal level is not caused by a significant physiological factor but by a factor that allows the monitoring to continue in the low signal monitoring mode. This kind of factor may be a motion of the patient, which may be detected by a motion artifact detector. FIG. 6 shows an optional motion artifact detection unit 69 adapted to detect baseline swings in the physiological signal. If a baseline swing, like the one shown in FIG. 2, is detected, a notification is supplied to the monitoring mode control unit 66 and/or to the user interface dialog unit 68, thereby to skip displaying the user interface dialog window. The user interface dialog unit may also be adapted to display a preferences menu through which the user may define in advance whether the decision to enter the low level monitoring mode may be made automatically in case low signal level and a baseline swing are detected substantially simultaneously, or whether a user confirmation is always needed.

It is to be noted that FIG. 6 illustrates the division of the functionalities of the control and processing unit in logical sense and in view of the selection of the monitoring mode. In a real apparatus the functionalities may be distributed in different ways between the elements or units of the apparatus. It is further to be noted that the low signal monitoring mode is used with respect to the parameter(s) derived from the physiological signal whose level and morphology is monitored. The above-described alarm suppression mechanism may be applied to one or more physiological signals obtained from the subject. Since one or more parameters may be derived from each physiological signal, the suppression may concern one or more physiological parameters.

A conventional patient monitor may be upgraded to enable the monitor to control the alarm generation in the above-described manner. Such an apparatus upgrade may be implemented, for example, by delivering to the monitor a software module that may contain the above functionality. The software module may be delivered, for example, on a data carrier, such as a CD or a memory card, or through a telecommunications network. However, since the patient monitor is normally provided with an alarm mechanism (normal alarm mode algorithm), the software module does not necessarily comprise more than the program product portions needed to introduce the low signal monitoring mode in the patient monitor.

Signal morphology may be determined in the normal monitoring mode too, especially if morphology information is needed continuously. In this embodiment, current signal morphology is stored as the reference morphology when the low signal monitoring mode is entered and the determination of the signal morphology is continued when normal monitoring mode is restored after low signal monitoring mode.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for controlling alarms in a physiological monitoring apparatus, the method comprising:
    observing a level of a physiological signal obtained from a subject;
    in response to detecting a change of the level of the physiological signal to a predetermined value range representing low signal values, determining signal morphology for the physiological signal, thereby to define a reference morphology for the physiological signal;
    prompting for user permission to continue monitoring, wherein the prompting is performed in response to the detecting;
    continuing to monitor the signal morphology when the physiological signal remains in the predetermined value range; and
    suppressing alarms when the signal morphology fulfills predefined criteria with respect to the reference morphology and the level of the physiological signal remains in the predetermined value range, wherein the monitoring and suppressing are performed conditionally depending on user response to the prompting.

2. The method according to claim 1, wherein the suppressing includes increasing sensitivity of the physiological monitoring apparatus.

3. The method according to claim 1, wherein the suppressing includes using a reduced escalation rate for alarm escalation.

4. The method according to claim 1, wherein the determining and monitoring include determining the signal waveform morphology based on a predetermined section of the physiological signal.

5. The method according to claim 1, wherein the determining and monitoring include determining the signal waveform morphology based on the physiological signal and at least one further physiological signal obtained from the subject.

6. The method according to claim 1, further comprising stopping the suppressing when the monitoring indicates that the signal morphology fails to fulfill the predefined criteria with respect to the reference morphology.

7. The method according to claim 1, further comprising stopping the suppressing when the observing indicates that the level of the physiological signal has returned to normal value range.

8. A physiological monitoring apparatus comprising:
    a signal level monitoring unit adapted to monitor a level of a physiological signal obtained from a subject;
    a morphology determination unit adapted to determine signal morphology for the physiological signal, thereby to define a reference morphology for the physiological signal;
    a morphology monitoring unit adapted to continuously monitor whether the signal morphology fulfills predefined criteria with respect to the reference morphology;
    an alarm mode control unit adapted to suppress alarms when the signal waveform morphology fulfills the predefined criteria with respect to the reference morphology and when the level of the physiological signal remains in a predetermined value range representing low signal values; and
    a user interface dialog unit adapted to display a user prompt for getting user input, wherein the user interface dialog unit is responsive to the signal level monitoring unit and wherein the morphology monitoring unit and the alarm mode control unit are conditionally responsive to the user input.

9. The apparatus according to claim 8, wherein the physiological signal is an ECG signal.

10. The apparatus according to claim 9, wherein the morphology determination unit is adapted to determine the signal morphology based on at least one QRS complex of the ECG signal.

11. The apparatus according to claim 8, wherein the physiological signal is a plethysmographic signal.

12. The apparatus according to claim 8, wherein the signal level monitoring unit is adapted to define baseline of the physiological signal and amplitude of the physiological signal in relation to the baseline.

13. The apparatus according to claim 8, wherein the alarm mode control unit is adapted to control sensitivity of the patient monitor.

14. The apparatus according to claim 8, wherein the alarm mode control unit is adapted to control alarm escalation rate.

15. The apparatus according to claim 8, wherein the alarm mode control unit is adapted to stop suppression of alarms when the signal waveform morphology fails to fulfill the predefined criteria with respect to the reference morphology.

16. The apparatus according to claim 8, wherein the alarm mode control unit is adapted to stop suppression of alarms when the level of the physiological signal returns to normal value range.

17. The apparatus according to claim 8, further comprising a motion artifact detection unit adapted to indicate when the user prompt is to be omitted.

* * * * *